United States Patent [19]

Wright

[11] 4,063,077

[45] Dec. 13, 1977

[54] SOLVENT PROGRAMMER CONTROLLER

[76] Inventor: Julian R. Wright, 3204 Rexford, Austin, Tex. 78723

[21] Appl. No.: 768,778

[22] Filed: Feb. 15, 1977

[51] Int. Cl.² .................. G01N 31/08; G06F 15/46
[52] U.S. Cl. .................................. 364/502; 210/31 C; 210/198 C; 235/92 FL; 364/497
[58] Field of Search ............ 235/151.12, 151.1, 151.3, 235/151.35, 151.34, 92 FL, 92 PD, 92 TF, 92 T, 92 FQ, 92 CT, 92 EV, 92 CC; 73/23.1, 61.1 C; 137/88, 101.19, 624.11, 624.12, 624.18, 624.2; 210/24 C, 31 C, 198 C; 55/271, 274, 67, 38 C; 23/230 R, 230 A, 253 R, 253 A

[56] References Cited

U.S. PATENT DOCUMENTS

| | | | |
|---|---|---|---|
| 3,121,160 | 2/1964 | Burk | 235/151.35 X |
| 3,267,264 | 8/1966 | Burk et al. | 235/151.35 |
| 3,592,045 | 7/1971 | Weiss | 73/23.1 |
| 3,600,563 | 8/1971 | Porter et al. | 235/92 FL X |
| 3,985,019 | 10/1976 | Boehme et al. | 73/61.1 C |

Primary Examiner—Joseph F. Ruggiero

[57] ABSTRACT

A controller for solvent programmer apparatus that produces programmed solvent mixtures for introduction to a liquid chromatographic analyzer. Under the direction of the controller, the solvent programmer accesses first and second solvents during a defined cycle of operation and proportions the solvents on the basis of the time within the cycle of operation that each solvent is accessed. The controller has a first counter that defines the cycle of operation and a second counter that is preset at the beginning of a cycle to a value representative of the percentage of the first solvent that is to be in a solvent mixture produced during the cycle. The second counter is then counted down. Output control logic responsive to the count states of the counters sends a command for the first solvent to be accessed upon the first counter reaching its maximum count, occurring at the beginning of a cycle, and sends a command for the second solvent to be accessed upon the second counter reaching its minimum count, with accessing of the first solvent being discontinued contemporaneously.

The value of the percentage of the first solvent is held in data storage means. In isochratic operation of the solvent programmer, the value stored remains fixed and is repeatedly loaded into the second counter. In gradient operation of the solvent programmer, a counter in the data storage means, after being preset to an initial percentage value, is counted up at some predetermined rate, with the new value stored being loaded into the second counter. The rate of change with time of the contents of the data storage means can be either linear or non-linear.

11 Claims, 9 Drawing Figures

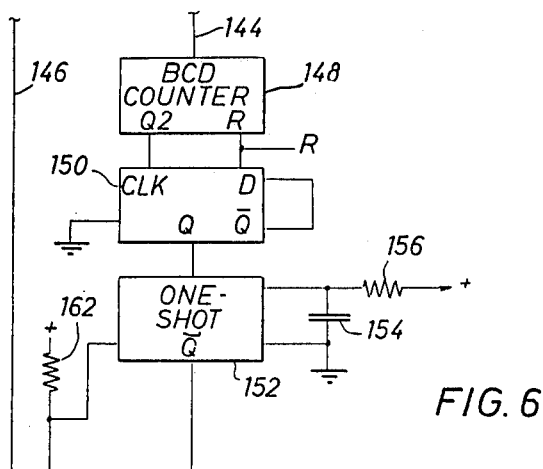
FIG. 6
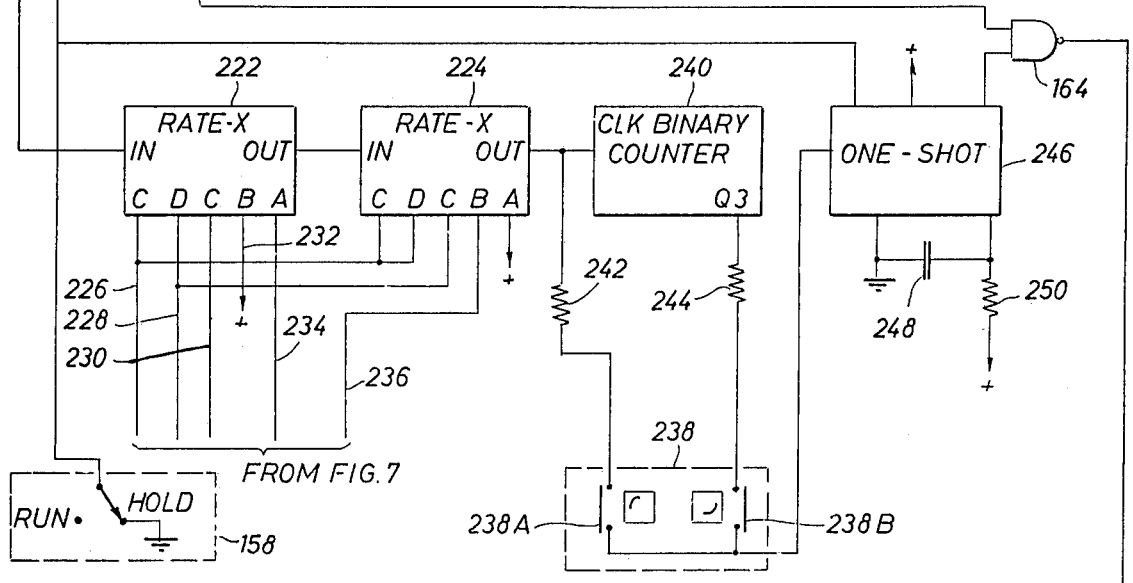
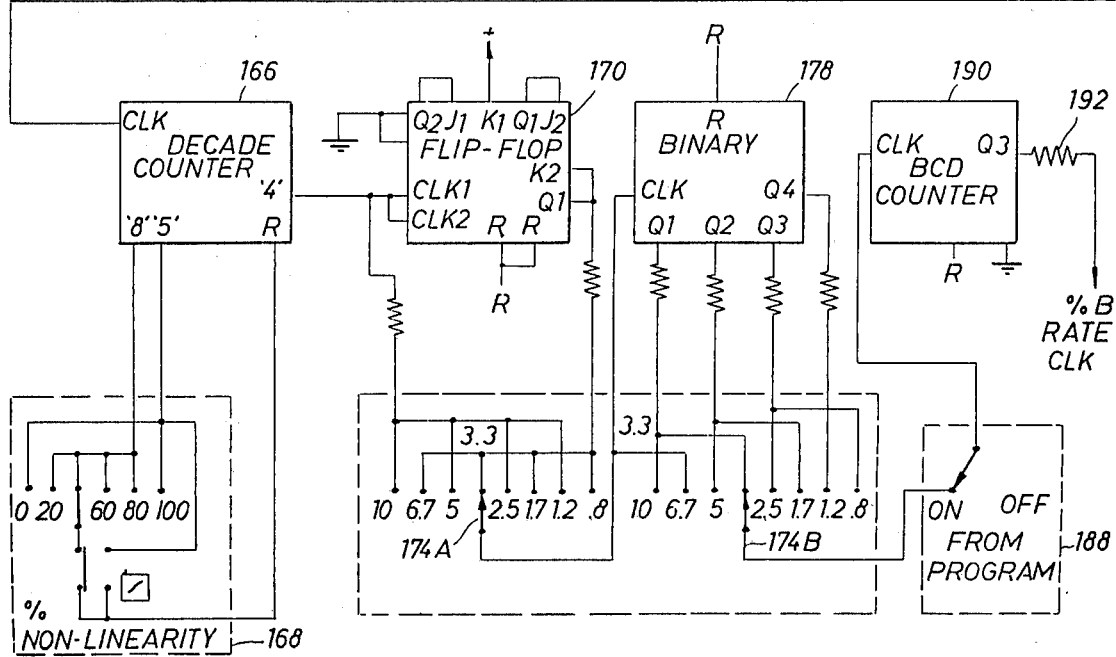

SOLVENT PROGRAMMER CONTROLLER

BACKGROUND OF THE INVENTION

The present invention relates to apparatus for controlling the operation of a solvent programmer that produces solvent mixtures for introduction to a liquid chromatograph; and more particularly, it relates to a controller that controls the operation of a solvent programmer to produce solvent mixtures comprised of two solvents proportioned on the basis of the portion of time within a defined interval that each solvent is accessed by an appropriate valve mechanism.

A common technique utilized to separate, isolate and identify the components of mixtures is that of chromatography. Basically, chromatography concerns a process that identifies the components of a mixture on the basis of differences in rates at which the individual components of the mixture migrate through a stationary medium under the influence of a mobile phase.

One particular type of chromatography is liquid adsorption chromatography frequently utilized in the separation of organic mixtures. In liquid adsorption chromatography, the stationary phase consists of a tubular column packed with an adsorbent material, with the sample being carried through the column by a solvent commonly referred to as the "carrier". The carrier is introduced into a chromatographic instrument by a pump. An equilibrium is established for the individual components of the sample according to its "attraction" to the stationary phase and its solubility in the carrier liquids. The rate at which a solute passes through the column of the chromatograph is dependent upon the equilibria existing, and separations occur where the distributions differ.

It is important in any type of liquid chromatography that a predetermined solvent percent or ratio be precisely maintained in the mixture that is presented to the chromatograph. Also, it is sometimes desired that the percentage of solvent in the mixture be varied with time in accordance with some predetermined gradient, which is often times referred to as a solvent program.

Although numerous techniques have been in use in past, a new technique for selectively producing a wide variety of programmed solvent mixtures for use in liquid chromatographic analysis has recently been developed. In accordance with this new technique, two solvents are mixed in prescribed proportions by a solvent programmer apparatus and made available to the inlet of a chromatographic analyzer. The solvent programmer apparatus produces the desired solvent mixture by proportioning the solvents on a time proportioned basis within a defined duty cycle. This new technique is disclosed in copending U.S. application Ser. No. 768,901 and assigned to the assignee of the instant application.

Solvent programmer apparatus in accordance with that disclosed in the referenced copending application comprises two modules. One is the solvent module which contains a valve mechanism adapted to access a separate liquid solvent from each of a plurality of sources, and be opened to any one of the sources. The other module is the control module containing a controller that is operably connected to the valve mechanism in the solvent module. The controller controls the valve mechanism to perform the various solvent programs, by operating the valve mechanism to access each of the solvent sources for a predetermined portion of a duty cycle of a prescribed duration of time.

Referring to FIG. 1, a solvent programmer 10 of the type described above is presented in diagram form. Two solvents labelled solvent "A" and solvent "B", generally designated by the reference numerals 12 and 14 respectively, are mixed in the proportion called for by the solvent programmer. The ratio of one solvent to the other is controlled by the action of a two-way valve 16 operated on a prescribed duty cycle. Either a fixed percentage of B running continuously, known as "isochratic" or "single solvent" operation, or a time varying percentage of B, known as "gradient" operation, may be derived. When a time-varying program is selected, the proportion of B in the mixture can be made to increase at a fixed rate, i.e., linear gradient, or at an increasing rate, i.e., convex gradient, or at a decreasing rate, i.e., concave gradient, by appropriate control of valve 16 during sequential duty cycles. In addition, the curvature of the two non-linear rates can be selected for several shapes between concave and convex.

As stated, the solvent programmer 10 consists of two modules, a control module 18 containing a controller necessary to operate valve 16 in the desired manner, and a solvent module 20. The solvent module contains the valve 16, a pump 22 for drawing solvent from each solvent source upon being accessed by the valve, a mixer 24, and a breather reservoir 26. Additional details of the solvent module 20 may be had by reference to copending application Ser. No. 769,901.

Referring next to FIG. 2, the various linear and non-linear time-varying solvent programs that can be carried out by the solvent programmer 10 are presented in a graph relating percentage of solvent B to time in minutes. As shown in the graph, a linear gradient program is provided by a constant rate of change of the percentage of solvent B. A convex gradient is formed by an increasing rate of change of percentage of solvent B, and a concave gradient by a decreasing rate of change. Each of the non-linear gradients shown in the graph represents a particular percentage of non-linearity. When a non-linear program is run, the elasped time from 0 to 100% B is approximately the same as for the linear gradient and is a function of the percentage of non-linearity chosen.

In isochratic operation, the valve mechanism is operated, within each successive duty cycle, to proportion the solvents in constant, non-varying proportions. To achieve this, the valve mechanism is opened to each solvent for the same portion of the duty cycle, during each duty cycle. Accordingly, for a mixture having 10% solvent B and 90% solvent A, during each duty cycle, the valve mechanism would by open to solvent A 90 percent of the duty cycle and to solvent B 10 percent of the duty cycle.

In linear gradient operation, the valve mechanism is operated to proportion the solvents in amounts that vary at a fixed rate of change over time in accordance with a program. To achieve this type of operation, the valve mechanism is opened to each solvent for a different portion of the duty cycle from one duty cycle to a later occurring one. Changes in the portion of a duty cycle that the valve mechanism is opened to each solvent are at a fixed rate as between duty cycles spaced apart in time. Accordingly, for a mixture that increases in the percentage of solvent B at a rate of 5% per minute, a duty cycle occurring one minute after a previous duty cycle will have the valve mechanism opened to solvent B for 5 percent more of the duty cycle time than it was for a previous duty cycle.

In non-linear gradient operation, the valve mechanism is operated to proportion the solvents in proportions that vary at a non-constant rate of change. The rate of change may be either increasing or decreasing. In this type of operation, the valve mechanism is opened to each solvent for a different portion of the duty cycle, from one duty cycle to a latter occurring one. However, changes in the portion of a duty cycle that the valve mechanism is opened to each solvent varies at a non-constant rate as between duty cycles spaced apart in time. That is, the amount of time within a duty cycle that the valve mechanism is opened to solvent B will change non-uniformly between duty cycles spaced apart in time. Accordingly, the apparatus of the instant invention can provide a solvent mixture that varies in the rate of change of one solvent to another over time.

In addition, the controller may operate the valve mechanism in the non-linear gradient mode to effect varying degrees of non-linearity in the program run by the apparatus.

The various solvent programs discussed above and illustrated in FIG. 2 are made possible by the control signals supplied by controller 28 (see FIG. 1) in control module 18. Controller 28 opens valve 16 to each of the solvent sources, A or B, on a time proportioned basis to produce the predetermined mixture of solvents. It was disclosed that, in a preferred embodiment, the valve mechanism is a multiple-way solenoid valve and the controller comprises electronic circuitry that provides the necessary electrical control signals to the solenoid valve.

Accordingly, the instant invention seeks to provide a suitable controller for use in a solvent programmer of the type disclosed in the referenced copending application.

SUMMARY OF THE INVENTION

According to the present invention, there is provided a controller for use in solvent programmer apparatus that produces programmed solvent mixtures for introduction to a liquid chromatographic analyzer, which analyzer produces a solvent mixture by accessing first and second solvents during a defined cycle of operation to proportion the same on the basis of the time within the cycle that each solvent is accessed. A controller in accordance with the present invention comprises a time base generator for generating a timing clock signal at a prescribed frequency which is then applied to first and second counters. The first counter defines the cycle of operation of the solvent programmer within which the solvents are proportioned. Data storage means is provided for holding the percentage value of the first solvent that is to be in a mixture produced by the solvent programmer. Output control logic responsive to the count value in the first and second counters causes the first solvent to be accessed when the first counter reaches a prescribed count that indicates the beginning of a cycle of operation. The output control logic then causes the second solvent to be accessed for the remainder of the cycle of operation upon the second counter reaching a prescribed count, which count is dependent upon the percentage value stored in the data storage means. Upon the second counter reaching the prescribed count, access of the first solvent is discontinued until the beginning of the next cycle of operation.

More specifically, a controller in accordance with the present invention comprises first and second counters which are an up counter and a down counter, respectively, with the down counter defining the portion of each cycle of operation that the first solvent is to be accessed by the solvent programmer apparatus. Also, the data storage means stores a digital representation of the percentage value of the first solvent that is to be in a mixture of the solvent produced by the solvent programmer during a cycle of operation. The output control logic is responsive to the maximum count of the up counter and to the minimum count of the down counter, and causes the digital representation stored in the data storage means to be loaded into the down counter during each cycle of operation.

In yet another aspect of the present invention, a controller in accordance with the present invention may be utilized to operate the solvent programmer apparatus to produce a solvent mixture wherein the proportions of the two solvents change with time. A controller in accordance with the present invention for providing solvent programmer apparatus operation of this type has data storage means which comprises a counter that increases the percentage value stored therein at a rate determined by the frequency of a clock signal that is supplied thereto. In the case of a linear rate of change of the solvent proportions, the controller further comprises a linear rate generator for generating the clock signal supplied to the counter in the data storage means, and frequency division circuitry having means for setting the frequency of the clock signal to thereby increase the stored value at a fixed predetermined rate.

In yet a further aspect of the instant invention, a controller is provided for use in a solvent programmer apparatus to operate the same to produce a solvent mixture that changes the proportions of the solvents on a non-linear time rate of change. A controller in accordance with the present invention for operating a solvent programmer in this manner further comprises a non-linear rate generator for generating a clock signal that may be applied to the counter in the data storage means. The non-linear rate generator varies the frequency of the clock signal according to the percentage value storaged in the data storage means. Accordingly, at certain percentage levels the rate of increase will itself be varied.

In a yet further aspect of the present invention, the controller can operate the solvent programmer apparatus in a variety of various non-linear gradient solvent mixtures. To provide such operation, the controller further comprises both a linear and a non-linear rate generator of the type defined above, with non-linearity control logic permitting the clock signal generated by each rate generator to be supplied to the counter in the data storage means on a timed duty cycle basis. More specifically, to increase the non-linearity of the gradient solvent the mixture being produced by the solvent programmer, the non-linearity control logic supplies the clock signal from the non-linear rate generator to the counter in the data storage means for an increasingly greater period of time than the clock signal from the linear rate generator.

Further in accordance with the present invention, a display unit may be provided which displays the percentage of the first solvent that is being placed in the solvent mixture being produced by the solvent programmer apparatus. To this end, the percentage value stored in the data storage means is applied to the display circuitry. Alternatively, the elapsed time of the solvent program run currently underway may be displayed on the display. The data for this readout is obtained from an elapsed time counter which counts the time in minutes that the solvent program run has been underway.

BRIEF DESCRIPTION OF THE DRAWINGS

A more complete appreciation of the invention may be had by reference to the accompanying drawings, illustrating a preferred embodiment of the invention to be described in detail, in which like reference numerals designate identical or corresponding parts throughout the several views and wherein:

FIGS. 4-9 are schematic diagrams of circuitry to implement the controller diagrammed in FIG. 3.

DETAILED DESCRIPTION OF THE PREFERRED EMBODIMENT

General System Diagram and Functions

Figure 3:
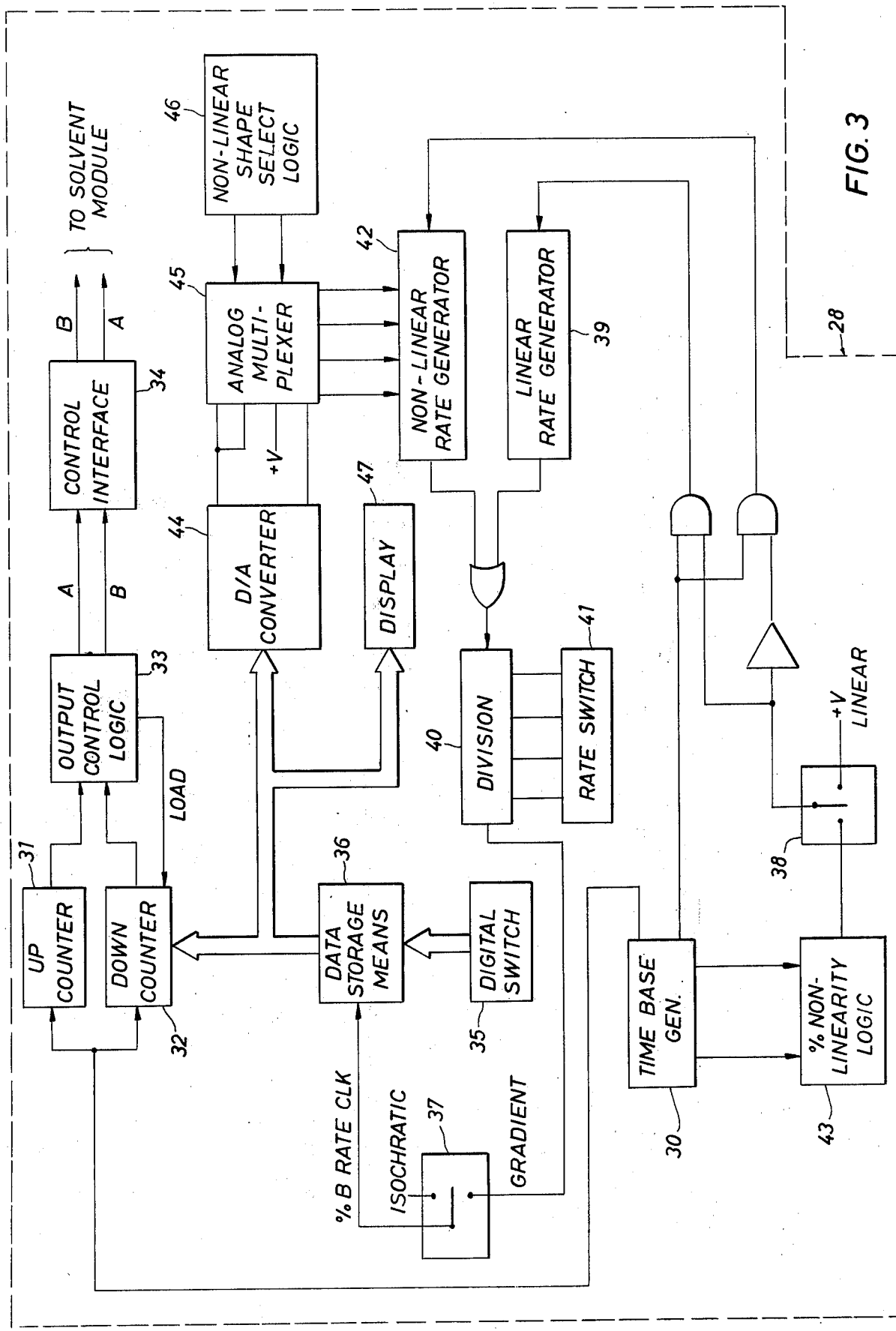
FIG. 3 is a block diagram representation of a controller in accordance with the instant invention.

Referring first to FIG. 3, there is presented a block diagram representation of a controller for use in a solvent programmer apparatus of the type previously described, wherein the controller provides control signals necessary to operate a valve mechanism to perform a wide variety of programmed solvent mixtures for use in liquid chromatographic analysis.

As controller 28 is capable of three modes of operation, the concepts of controller operation will be described in the context of the particular modes of operation. The three modes of operation are the isochratic operation, linear gradient operation, and non-linear gradient operation.

Isochratic operation, it will be recalled, is that operation wherein a solvent mixture is produced continuously having fixed proportions of one solvent to the other. In controller 28 illustrated in FIG. 3, operation will be such that a mixture having a fixed percentage of solvent B will be continuously provided by the solvent programmer to a chromatographic analyzer.

As has been mentioned previously in the background discussion of the instant invention, the ratio of solvents is controlled by the action of a solenoid valve in the solvent module operating on a fixed duty cycle. Accordingly, it is within this time span that the solvents A and B are proportioned according to the amount of time within the cycle that the solenoid valve is opened to each. Operation of the solvent programmer proceeds continuously, therefore a controller must be provided to develop the appropriate time slots within which operation of the valve is conducted. It will be appreciated that to have continuous solvent mixture production, the controller operation must proceed on the basis of a succession of individual controller cycles of operation. The cycle of operation, or duty cycle, within which the controller operates is defined by time base generator 30 which produces the necessary timing signals. The frequency of the time base signal generated in time base generator 30 will depend upon the desired duration of the cycle of operation.

The time base signal is applied to first and second counters 31 and 32, which are preferably an up counter and a down counter, respectively. Both counters 31 and 32 provide signals to output control logic 33 which developes digital control signals. Control interface 34 is responsive to the logic control signals available from output control logic 33 and develops signals that are supplied to the solvent module of the solvent programmer that are compatable with the type of solvent accessing mechanism utilized therein. Typically, the control interface will develop valve actuation voltages on the basis of the logic control signals to operate solenoid valves that access the solvents.

Prior to a solvent programmer run, the percentage of solvent B desired to be maintained during the isochratic operation is set in digital switch 35. At the beginning of a solvent programmer run, counters 31 and 32 are reset and the digital representation set in digital switch 35 is entered into and stored in data storage means 36. In isochratic operation, when counter 31 reaches a prescribed count, preferably its maximum count, a signal indicative the condition is provided to output control logic 33. Receipt of this signal by output control logic 33 causes a digital control signal to be applied to control interface 34, resulting in a valve actuation voltage being developed for energizing the B valve in the solvent module and permitting solvent B to be drawn from its container at a constant rate by a pump or the like. Simultaneously, output control logic 33 supplies a signal to counter 32 causing the digital representation stored in data storage means 36 to be loaded thereinto.

Counter 31 continues to count up with each pulse received from the time base generator 30, while counter 32 counts down with each pulse received. At a prescribed count, preferably the minimum count or zero, a signal is initiated from counter 32 and applied to output control logic 33. A control signal is issued from control logic 33 to control interface 34, which causes the valve in the solvent module to access solvent A. Also, internally of output control logic 33, the control signal that results in the energization of the valve to access solvent B is disabled. Accordingly, only solvent A is allowed to be drawn by the pump into the solvent module.

Solvent A continues to be accessed until counter 31 again reaches its maximum count, whereupon the sequence of operations discussed above will be repeated. It will be appreciated that the frequency of the time base signal available from time base generator 30 and prescribed count that counter 31 must reach in order to generate the signal supplied to control logic 33 will determine the duration of the controller cycle of operation.

In addition to isochratic operation, controller 28 is able to produce a time-varying percentage of solvent B in a mixture, which operation is referred to as gradient operation. When either of the gradient modes of operation are selected, as determined by the setting of switch 37, the digital representation of the percentage of B contained in data storage means 36 will be allowed to be altered. In isochratic operation, the digital representation stored in data storage means remains the same. In order to permit a changing value of percentage of solvent B in data storage means 36, some type of counter must be used which is clocked at a certain rate depending upon the rate of increase of percentage B desired.

Gradient operation may be in either a linear or a non-linear mode, depending upon the setting of switch 38. In performing linear gradient operation, controller 28 continues to operate on a prescribed cycle of operation. Accordingly, the block functions described in connection with isochratic operation of the controller are utilized and operate in essentially the same manner. However, rather than repeated loading of the same value of percentage of solvent B into counter 32, new values of the percentage of solvent B are loaded in during later occurring cycles of operation, such that the portion of time within each cycle of operation that solvents A and B are selected are altered accordingly.

The increasing value of the percentage of solvent B that is loaded into counter 32 is obtained from counters in state of storage means 36. After an initial percentage of solvent B is loaded into data storage means 36 from digital switch 35, the counters therein are counted up at a rate which is determined by the desired increase per minute of solvent B percentage. To advance counters in data storage means 36, % B RATE CLK is supplied thereto.

In the linear gradient mode of operation, a second timing signal derived from time base generator 30 is applied to linear rate generator 39 which divides the frequency down and produces a train of pulses that are applied to a division block 40 to further divide the frequency of the signal in accordance with the setting of rate switch 41. The various division factors that may be applied in block 40 permit several different frequencies of % B RATE CLK to be applied to the counters in data storage means 36, thereby permitting a variety of percentage of solvent B increases to be achieved.

Operation in the linear gradient mode proceeds as in the isochratic mode in that each cycle of operation is proportioned into two segments, the length of each being dependent upon the amount of time that solvent A or solvent B is to be accessed by the solvent module.

The remaining mode of operation is that of the non-linear gradient mode. In this mode, the percentage of solvent B increases with time at a non-constant rate of change. The rate of change may be either increasing or decreasing, which changes in the portion of a cycle of operation that solvent B is selected being at a non-constant rate as between duty cycles spaced apart in time.

Operation in the non-linear gradient mode is similar to linear gradient operation; however, % B RATE CLK causes the counters in data storage means 36 to be counted up at a non-uniform rate. To achieve such operation, % B RATE CLK is a combination of clock signals from linear rate generator 39 and non-linear rate generator 42. The same timing signal from time base generator 30 is applied to each rate generator on a timed duty cycle basis. The amount of time that each rate generator receives the timing signal is determined by percentage non-linearity logic 43.

Non-linear rate generator 42 receives control signals, the value of which determines the division factor that is applied to the timing signal through that function block. The control signals are based upon the then existing value of percentage of solvent B, as represented by the digital value in data storage means 36 and applied to D/A converter 44. An analog threshold detector 45 under the direction of non-linear shape select logic 46 determines whether the non-linear rate generator will produce a division sequence to provide an increasing rate of change of percentage of solvent B or a decreasing rate of change percentage of solvent B.

It will also be noted from the diagram in FIG. 3 that a display 47 is provided to display the percentage of the mixture that is comprised of solvent B. The display produces such indication based upon the digital representation stored in data storage means 36.

Preferred Circuit Configurations

Figure 1:
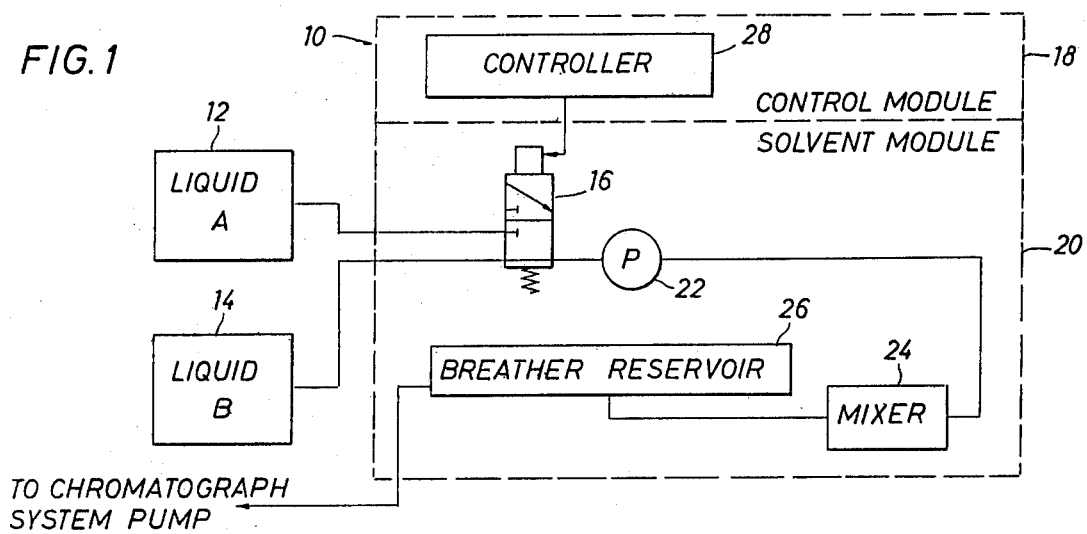
FIG. 1 is a general system diagram of a solvent programmer apparatus in which the instant invention may be utilized.
Figure 4:
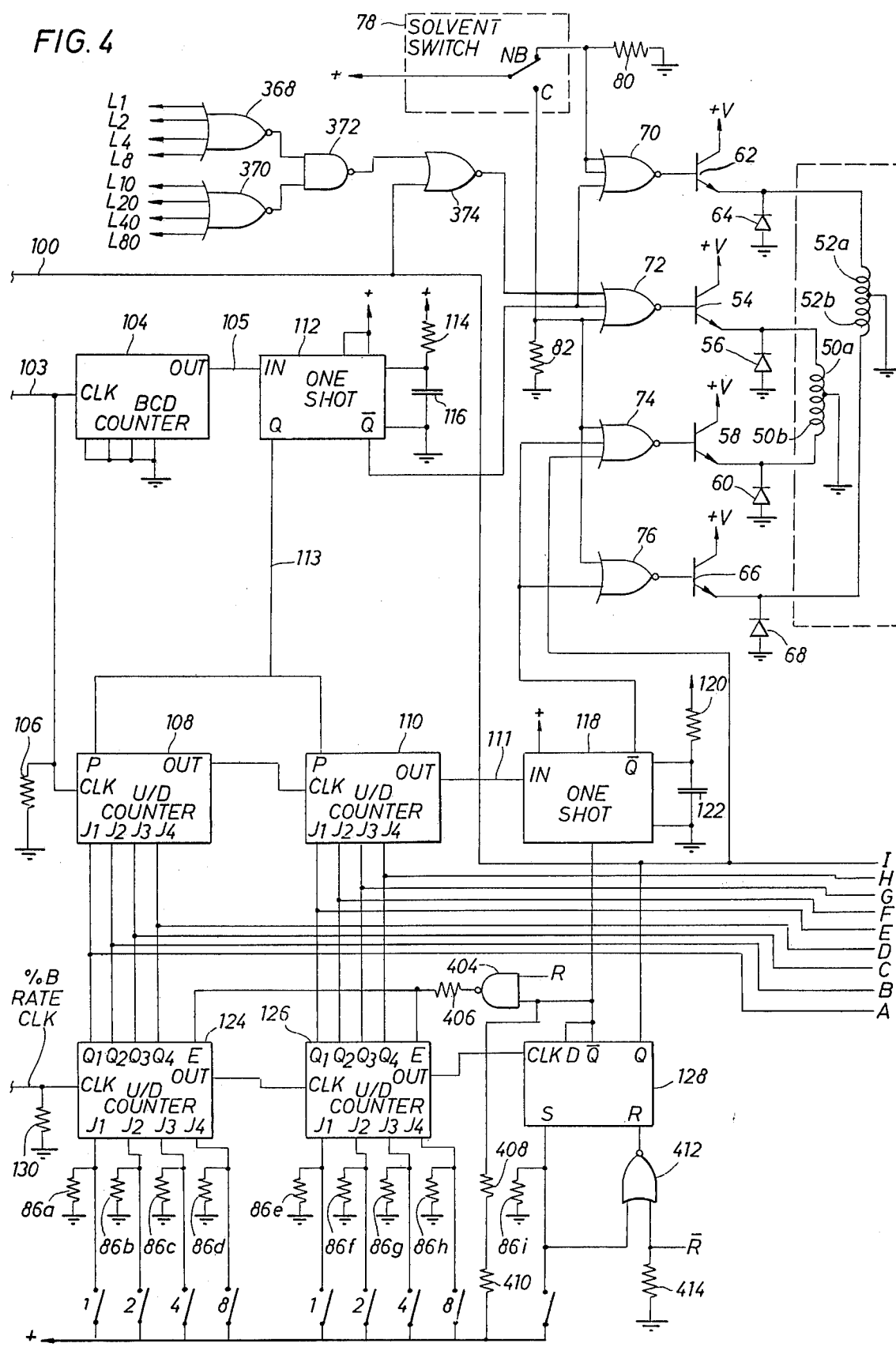

Referring to FIG. 4, center-tapped coils 50, 52 of solenoid valves 16 and 38, respectively, are shown, though physically located in the solvent module of the solvent programmer illustrated in FIG. 1. Coils 50 and 52, being center-tapped coils, each, in effect, constitute two separate solenoid coils. Accordingly, the upper portion of coil 50 will be referred to as coil 50a and the lower half of coil 50 will be referred to as 50b. Coil 52 will be referred to in a similar fashion. Because coils 50 and 52 are actually each two separate coils, a separate driver circuit for each end of the coils is required. Accordingly, coil 50a is connected to the emitter of transistor 54, with diode 56 being shunted across coil 50a to protect against back emf developed during switching. Similarly, coil 50b is connected to the emitter of transistor 58, with diode 60 shunted thereacross. Transistor 62 is the driver for coil 52a, and diode 64 is shunted across that coil. Finally, transistor 66 is the driver for coil 52b, with diode 68 shunted across that coil.

Driver transistors 54, 58, 62 and 66 constitute control interface 34, which controls the various solenoid valves, and is responsive to logic command signals received from output control logic 33 which comprises NOR gates 70, 72, 74 and 76. The outputs of these gates are connected as shown to the base of a separate one of the driver transistors. Based upon the logical input signals applied to the NOR gates, the appropriate logical output state is produced.

Primary control of the solenoid valves is by solvent switch 78 which provides a logic input to NOR gates 70–76. If solvent switch 78 is at the A/B position as shown, positive power supply voltage, or a logic "1", is applied as an input to NOR gate 70; driver transistor 62 is turned off and no current flows through coil 52a. Valve 38, which controls the flow of solvent C, an alternative flushing solvent, is turned to the off position, and solvent C does not flow into the chromatographic system.

With solvent switch 78 in the A/B position, a logic "0" is applied as input to NOR gates 72, 74 and 76 by virtue of those inputs being connected to ground potential through pull-down resistor 82. Although this single input does not by itself control the output signal from each of the NOR gates, it nonetheless serves to enable operation of those gates, as determined by the logic signals applied to the other inputs of each gate.

If solvent switch 78 is at the C position, positive power supply potential, or a logic "1", is applied as an input to NOR gates 72, 74 and 76, thereby disabling these gates and maintaining their output at a logic "0", which of course will keep driver transistors 54, 58 and 66 in the turned-off state. NOR gate 70 will, however, have ground potential applied as an input through resistor 80. With a logic "0" applied as an input to NOR 70, that gate will be enabled with the logic value existing at the output of NOR gate 70 being determined by the remaining input signal. The remaining control signals that are applied as inputs to NOR gates 70, 72, 74 and 76, will be discussed fully later herein as the description of the circuitry for controller 28 continues.

Digital switch 35 comprises a set of "on-off" switches 84 and is used to set the isochratic percentage desired. Specifically, switch 35 can be digital thumb switch which provides a binary representation of the desired percentage of liquid B. Switch 35 is divided into three sections to provide ones, tens, and hundreds in order that any percentage between 0 and 100% may be set. As shown, one pole of each switch is connected to the positive power supply potential, which serves as a logic "1", with the other pole of each switch being connected through a respective resistor 86a-i to ground potential. If a particular switch is opened, a logic "0" will be presented as the value of that binary digit; but if that switch is closed, then a logic "1" will be provided as the value of the binary digit.

As has been mentioned previously in the general discussion, the ratio of solvents is controlled by the action of solenoid valve 16 operating on a three second duty cycle. Accordingly, it is within this time span that the solvents A and B are proportioned, according to the amount of time within the cycle that solenoid valve 16 is opened to each. Operation of the solvent programmer 10 proceeds continuously, therefore circuitry must be provided to develop the appropriate time slots within which operation of the valve is conducted.

Figure 5:
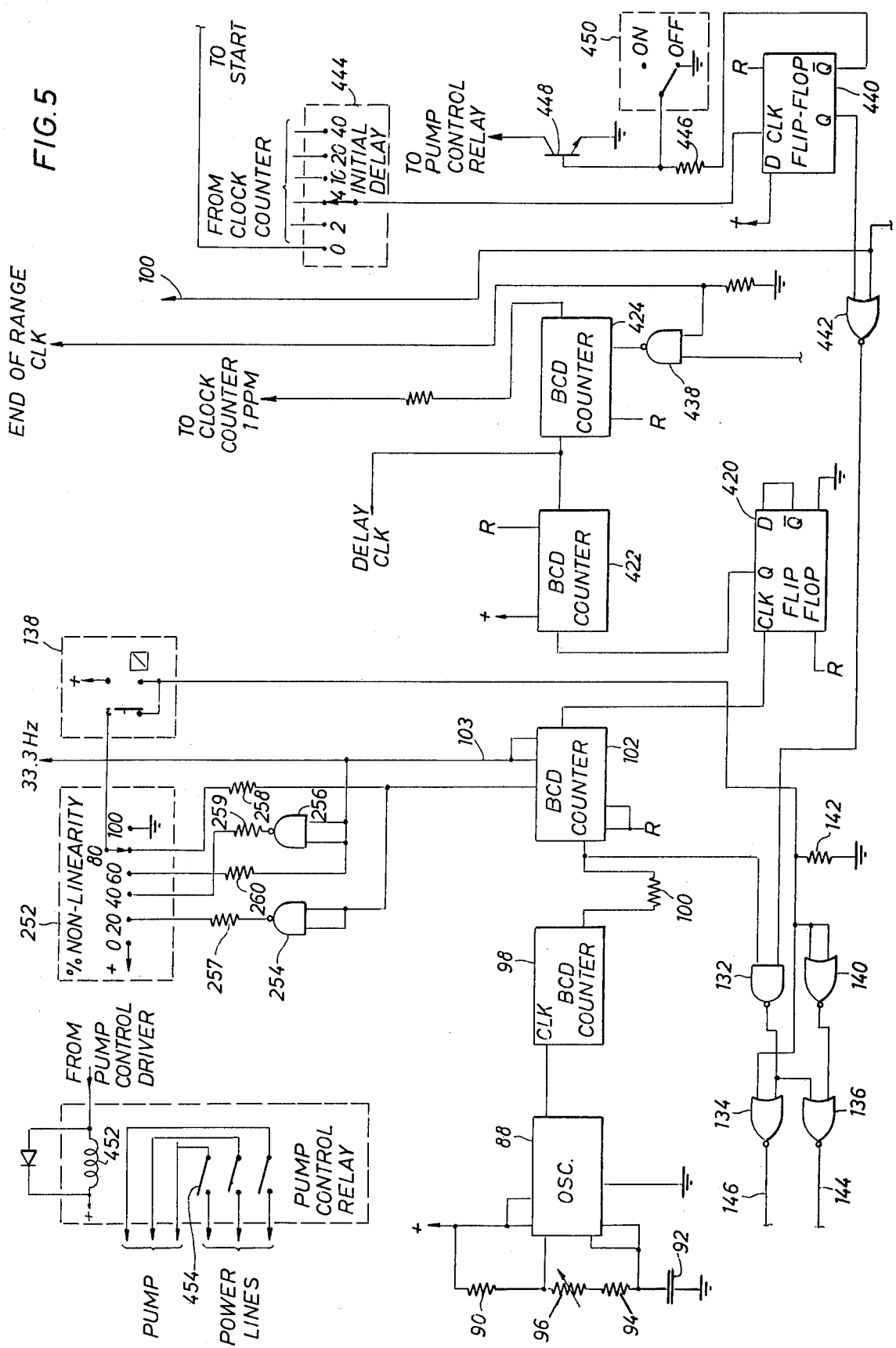

With reference to FIG. 5, the time base generator 30 for deriving the necessary timing signals is presented. The time base signal is generated by an oscillator circuit 88, the free-running frequency and duty cycle of which are accurately controlled by resistor 90, capacitor 92 and the series combination of resistor 94 and variable resistor 96. Oscillator circuit 88 produces a 3.33 KHz frequency signal which is applied to BCD counter 98 and is divided down to 333 Hz. The output frequency from counter 98 is applied through resistor 100 to another BCD counter 102 which divides the frequency down to 33.3 Hz. The signal is made available over line 103.

Returning again to FIG. 4, the 33.3 Hz input signal available on line 103 is applied to BCD counter 104 which divides the signal by 100 to produce a 0.333 Hz signal. The 33.3 Hz signal is applied to resistor 106 and presettable up/down counter 108 connected as a decade counter to count in the down mode. The carry out line 109 from up/down counter 108 connects to the clock input on cascaded up/down counter 110, which is also connected as a decade counter to count in the down mode. In combination, counters 108 and 110 form a two-decade counter.

The 0.333 Hz signal available on line 105 from BCD counter 104 provides a clock signal that completes one cycle in three seconds. That signal is used to trigger one-shot 112, the output of which is on the $\overline{Q}$ output. The value of the $\overline{Q}$ output is applied as a logic signal to NOR gates 70 and 72 to control the output state of each of those gates. The output signal available from one-shot 112 is in the form of an accurate output pulse, the duration and accuracy of which are determined by the external timing components, resistor 114 and capacitor 116.

The carry out signal available on line 111 from up/down counter 110, signifying count "0", is applied to one-shot 118 which generates a pulse from the $\overline{Q}$ output. The pulse characteristics are determined by the external timing components of resistor 120 and capacitor 122. The pulse available from one-shot 118 is applied as a logic input signal to NOR gates 74 and 76.

The percentage of liquid B desired to be maintained during the isocratic operation is, as mentioned before, set by digital switch 84. The digital representation of the desired percentage of B is entered into and stored in up/down counters 124, 126. In the isocratic operation mode, counters 124 and 126 maintain the value of the percentage B set by the digital switch 84, and are not allowed to count. The binary value of the percentage of solvent B desired is made available from counters 124 and 126 on their Q output lines. The hundreds designation is stored in D-type flip-flop 128. The ones and tens representations are, of course, stored in counters 124 and 126, respectively.

In operation, when BCD counter 104 reaches the count of 100, one-shot 112 is triggered, producing a negative-going pulse at the $\overline{Q}$ output. This pulse, constituting a logic "0" input signal, is applied as an input to NOR gates 70 and 72. With solvent switch 78 in the A/B position, a logic "0" is applied to the input lead of NOR gate 72 connected to resistor 82; and accordingly, the output line of NOR gate 72 will go to a logic "1". Driver transistor 54 will be turned-on, sending current through coil 50a causing solenoid valve 16 to open to the solvent B. At the same time, a positive-going pulse will be sent from the Q output of one-shot 112. This pulse is transmitted over line 113 to the preset inputs of both counters 108 and 110 to simultaneously load counters 108 and 110 to the value of percentage B stored in counters 124 and 126. With each succeeding pulse of the 33.3 Hz signal on line 103, counters 108 and 110 count downward; and at the count of zero, a pulse is sent from counter 110 over line 111 to trigger one-shot 118. A negative-going pulse is generated by one-shot 118 and made available from the $\overline{Q}$ output. This signal, a logic "0", is applied to NOR gates 74 and 76. The other inputs to these two gates are already at logic "0"; and therefore, the output of each gate will go to a logic "1". By turning-on driver transistor 58, current flows through coil 50b in a direction opposite to that in which current previously flowed through coil 50a, thereby turning solenoid valve 16 away from solvent B to solvent A, permitting that liquid to be drawn by the continuous pump into the solvent module. BCD counter 104 continues to count up, while counters 108 and 110 continue to count down. When counter 104 again reaches 100, the sequence of operation is repeated.

By way of example, assume that the value of percentage B in a mixture is desired to be maintained at 10%. The digital switch 84 would be set to the value of 10, and the binary representation of that percentage would be entered into and stored in counters 124 and 126. When counter 104 reaches the count of 100, solenoid valve 16 is turned to allow solvent B to be drawn into the solvent module. Ten counts later, counters 108 and 109 reach a count of zero, and solenoid valve 16 is turned to permit solvent A to be drawn into the solvent module. The valve will remain in this position until counter 104 again reaches the count of 100, which will of course require 90 additional counts. It is therefore evident that solenoid valve 16 is turned to permit the introduction of solvent A for 90 counts, while the valve is turned to permit the introduction of solvent B for 10 counts. Accordingly, the result is that the desired mixture of 10% solvent B and 90% solvent A composition is attained.

It will be appreciated that the duty cycle within which the solvents are proportioned is the time that it takes two-decade counter 104 to count to 100. Since the input clock signal is 33.3 Hz, the time required for counter 104 to reach the count of 100 is 3 seconds.

Figure 2:
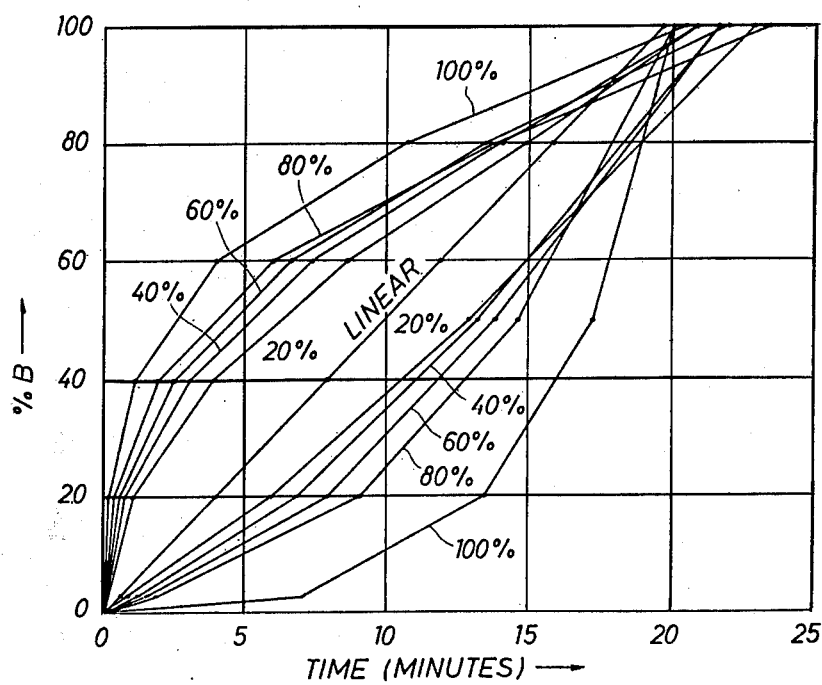
FIG. 2 is a graph illustrating the shape of the various linear and non-linear time-varying solvent programs that may be provided by the apparatus diagrammed in FIG. 1.

When a linear gradient program is selected, the amount of solvent B is increased at a fixed rate. The graph in FIG. 2 illustrates but one linear gradient program in which the percentage of solvent B in the mixture increases at the rate of 5% per minute. The table below gives a full listing of the available linear solvent programs which controller 28 can provide.

TABLE A

| %B PER MINUTE | SECONDS TIME PER 1% | MINUTES FOR TOTAL GRADIENT |
|---|---|---|
| 0.83 | 72 | 120 |
| 1.25 | 48 | 80 |
| 1.67 | 36 | 60 |
| 2.50 | 24 | 40 |
| 3.33 | 18 | 30 |
| 5.00 | 12 | 20 |
| 6.67 | 9 | 15 |
| 10.00 | 6 | 10 |

In performing linear gradient operation, controller 28, rather than repeatedly loading the same value of percentage solvent B into up/down counters 108 and 110, loads a different percentage of solvent B during subsequent cycles of operation, such that the portion of time within each duty cycle that solenoid valve 16 is open to solvent A or B is altered accordingly.

The increasing value of percentage of solvent B that is loaded into up/down counters 108 and 110 is obtained from counters 124 and 126. In isocratic operation, these counters are loaded from switch 35 with the percentage of solvent B that is desired to be maintained in the mixture. In linear gradient operation, however, after an initial percentage of solvent B is loaded into counters 124 and 126, which initial value is that value set by digital switch 84, counters 124 and 126 are counted up at a rate which is determined by the desired increase per minute of solvent B percentage. To advance counters 124 and 126, % B RATE CLK is supplied to counter 124 and pull-down resister 130.

With reference to FIGS. 5 and 6, the circuitry for generating the % B RATE CLK will be described. To generate this signal, the 333 Hz signal available from counter 98 via resistor 100 is applied to NAND gate 132 and passes therethrough to NOR gates 134 and 136. In the linear rate programs, NOR gate 136 is enabled by switch 138, which applies a logic "1" input to NOR gate 140. Gate 140 acts as an inverter, with resistor 142 serving as a pull-down resistor for both NOR gate 140 and 134. The 333 Hz clock signal being passed by NOR gate 136 is supplied over output line 144 to BCD counter 148 which divides the frequency down to 33.3 Hz. The output frequency from counter 148 is sent from the $Q_2$ output to flip-flop 150 to further divide the frequency by two and produce a 16.7 Hz signal, available at the Q output thereof. The 16.7 Hz signal is then applied to one-shot 152 to trigger the same, producing and an output pulse at the $\overline{Q}$ output. The duration of the pulse is determined by the external timing components capacitor 154 and resistor 156. Pulses from one-shot 152 may be stopped by interrupt switch 158 which applies a logic "0" signal to control lead 160 when the switch is in the HOLD position, and applies a logic "1" via resistor 162 when the switch is in the RUN position.

The pulse available from the $\overline{Q}$ output of one-shot 152 is applied to NAND gate 164 and is passed therethrough to a series of counters, which constitute division block 40 in FIG. 3, beginning with decade counter 166 having 10 decoded outputs available. The ten decoded outputs are normally low, that is a logic "0", and go high to a logic "1" at their respective decimal time slot. For linear gradient operation, decade counter 166 is connected to divide by five, with the output signal being taken from the decoded "4" output. The decoded decimal outputs "8" and "5" connect to percentage non-linearity switch 168 which, when operation is in the linear gradient mode, applies a reset signal from the decoded "5" output to the reset input on counter 166.

The output frequency from decade counter 166 is applied next to dual J-K flip-flop 170 and is also applied via resistor 172 to rate switch 174 (switch 41 in FIG. 3). Flip-flop 170 provides additional frequency division, with a divided down signal being available from the $Q_1$ output and applied to rate switch 174 through a resistor 176.

Binary counter 178 receives a signal from a rate switch 174, the frequency of which signal is determined according to the position of switch 174A. Binary counter 178 is a multiple stage counter having several output lines, each providing a different frequency. The signal available from the $Q_1$ output is applied to switch 178A via resistor 180, with the frequency signals available from outputs $Q_2$, $Q_3$, and $Q_4$ being applied to switch 174 in a similar manner via resistors 182, 184 and 186.

The signal available from rate switch 174 to flow program switch 188 is determined by the amount of division that takes place through flip-flop 170 and binary counter 178. The division ratio in these two counters is controlled by the setting of rate switch 174. The setting of rate switch segments 174A and 174B determine the slope of the linear gradient and determine which gradient program will be performed. The various linear gradients available are those set forth in TABLE A above. As will be noted from a close inspection of the connections to rate switch segment 174A, flip-flop 170 is utilized in the 6.7, 3.3, 1.7 and 0.8 percent per minute positions, with the output of decade counter 166 being used directly in the 10, 5, 2.5 and 1.2 percent per minute positions. The division performed by flip-flop 170 is by a factor of three, and the division performed in binary counter 178 is one for 6.7% per minute operation, two for 10 or 3.3 percent per minute operation, four for 5 or 1.7 percent per minute operation, eight for 2.5 or 0.8 percent per minute operation and 16 for 1.2 percent per minute operation.

The properly divided signal applied to flow program switch 188 is next applied to BCD counter 190 which further divides the frequency by 10 and supplies it via resistor 192 to up/down counter 124 shown in FIG. 4.

In the example shown, rate switch 174 is set to the 3.3 percent per minute position. In this situation, the 16.7 Hz signal coming through NAND gate 164 is divided by 5 in decade counter 166, by 3 in flip-flop 170, by 2 in binary counter 178, and by 10 in BCD counter 190. This results in a percentage rate clock frequency of 3⅓ pulses per minute, or an increase of 3.33 percent of solvent B per minute.

Operation in the linear gradient mode proceeds as in the isocratic mode in that each three second cycle of operation is proportioned into two segments; the length of each being dependent upon the amount of time that the valve is to be opened to solvent A or solvent B. In fact, linear gradient operation can be observed to be a series of successive isolated isocratic operations, each being carried out at a different, higher percentage of solvent B. This could be illustrated by connecting the output lines of counters 124 and 126 and flip-flop 128 to a suitable digital-to-analog converter.

Figure 7:
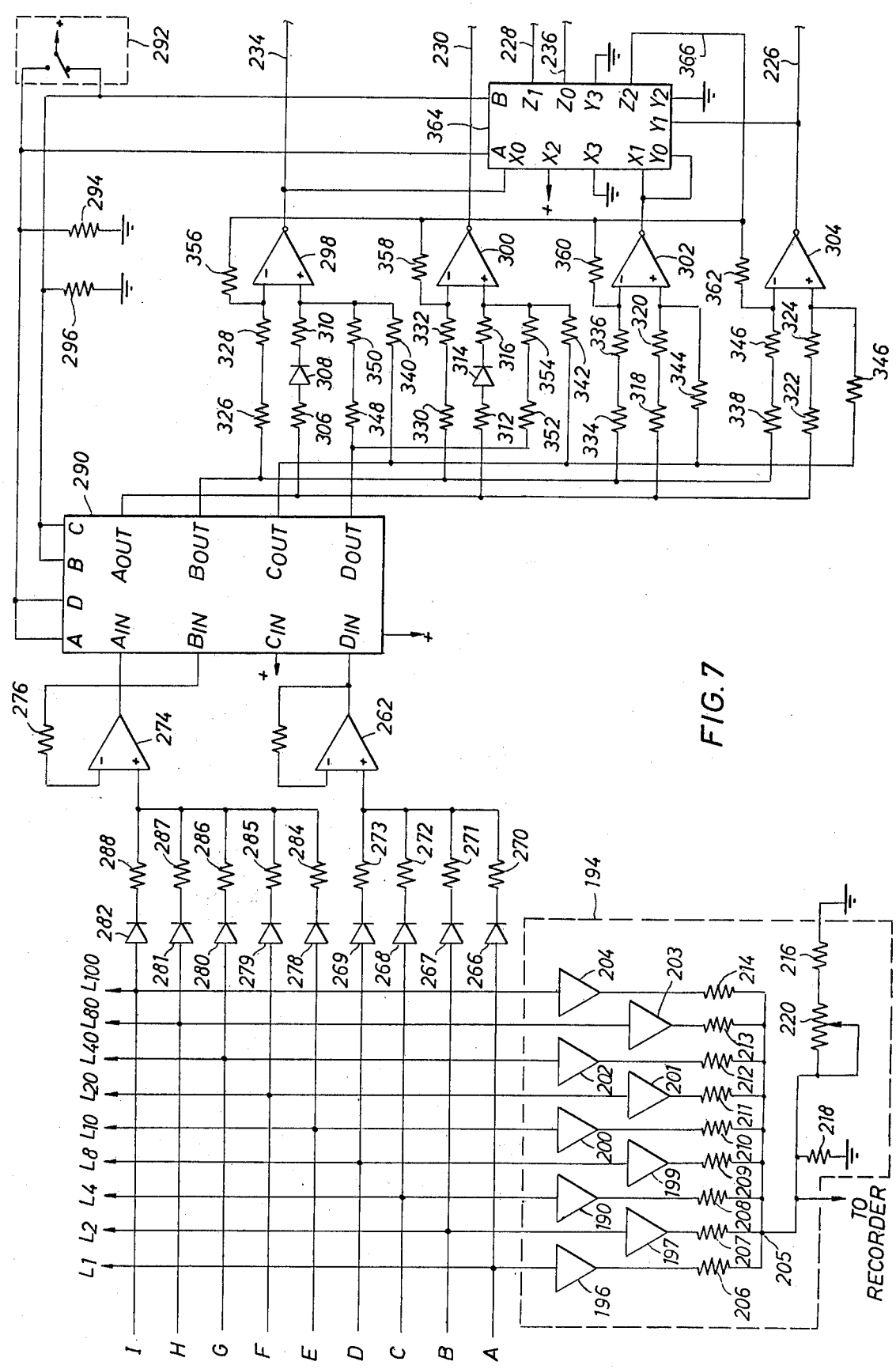

A suitable D/A converter is shown in FIG. 7 and designated generally by the reference numeral 194. Specifically, the digital representation of the percentage of solvent B set in counters 124, 126 and in flip-flop 128 are supplied via bus lines A-I to drivers 196-204. The output of each driver is connected to a common junction point 205 through a separate resistor each of which is a different value to provide a "weighted" value at the junction 205. Level adjustment is provided by a resistive network comprising resistors 216, 218 and variable resistor 220. The output of the digital-to-analog converter 194 is taken from the junction point 205. During linear gradient operation, the signal available to a strip chart recorded would result in a plot consisting of a series of step functions, with each step being of a specified amount. Thus, the recorder trace rather than being a straight line as shown in the graph of FIG. 2, would instead be a stair-step plot.

Controller 28 permits the selection of two gradient shapes in addition to the linear gradient described above. One is a convex gradient formed by an increasing rate of change of percentage B, and the other is a concave gradient formed by a decreasing rate of change of percentage B. The convex and concave gradients are non-linear gradients which may be further varied as to the degree of non-linearity. These various programs are illustrated in the graph in FIG. 2. In the non-linear gradient mode of operation, % B RATE CLK applied to up/down counter 124 is generated in a manner different from that in the linear gradient operation mode.

Referring first to FIG. 5, with switch 138 in the non-linear mode, both NOR gates 134 and 136 are able to pass pulses received from NAND gate 132. The pulses supplied from NOR gate 134 are available over line 136, and as described previously, pulses from NOR gate 136 are available over line 144. Referring next to FIG. 6, the signal available over line 146 is applied to cascaded BCD rate multipliers 222 and 224 which provide an output pulse rate based upon a binary coded decimal input number. For example, if six is the binary coded decimal input number, there will be six output pulses for every 10 input pulses. The binary coded decimal input number is supplied to rate multipliers 222 and 224 over lines 226, 228, 230, 232, 234 and 236. The manner in which the binary coded decimal input number is generated will be described further on herein.

Depending upon whether an increasing rate of change of percentage B or a decreasing rate of change of percentage B is desired, as determined by switch 238A and 238B, the ouput from rate multiplier 224 is either applied to binary counter 240 or bypassed therearound through resistor 242 and switch 238A. The output frequency signal from binary counter 240 is available through resistor 244 and switch 238B. The signal, whether coming directly from rate multiplier 224 or from binary counter 240, is supplied to one-shot 246 which produces a pulse train in accordance with the external timing components capacitor 248 and resistor 250. The pulse train from one-shot 246 may, however, be inhibited by interrupt switch 158.

Referring once again to FIG. 5, the connection arrangement for percentage non-linearity switch 252 is illustrated. Switch 252 is a multiple position switch which is set to the desired position depending upon the percentage on non-linearity desired. Switch 252 connects to switch 138 to pass the signals therethrough to NOR gates 134 and 136 to control the same and regulate the pulses through each. When zero percentage non-linearity is chosen, switch 252 will be connected to the positive power supply potential, and will in effect produce the same operation as though a linear gradient were selected. When a percentage non-linearity other than 0 or 100% is chosen, pulses are passed alternately through NOR gates 134 and 136 to the linear rate generator 39 and the non-linear rate generator 42. To clarify, the linear rate generator comprises counter 148, flip-flop 150 and one-shot 152. The non-linear rate generator comprises rate multipliers 222, 224, binary counter 240, and one-shot 246.

Passage of pulses through NOR gates 134 and 136 is controlled by % non-linearity logic 43 comprising BCD counter 102 and NAND gates 254, 256, which serve as inverters. Specifically, the $Q_2$ output of counter 102 connects through NAND gate 254 and resistor 157 to the 20% non-linearity position on switch 252. The output signal available from the $Q_2$ output of counter 102 is also made directly available through resistor 258 to the 80% non-linearity position on switch 252. The output signal available from the $Q_3$ output of counter 102 is supplied through NAND gate 256 and resistor 259 to the 40% non-linearity position on switch 252. The output signal from the $Q_3$ output of counter 102 is directly applied through resistor 260 to the 60% non-linearity position on switch 252. Depending upon the position of switch 252, the inverted or direct signal available from either the $Q_2$ or the $Q_3$ output of counter 102 is utilized to permit passage of pulses through NOR gates 134 and 136.

The selected signals directly from counter 102 control the switching of NOR gates 134 and 136 to provide duty cycles of 20 and 40%. Inversion through NAND gates 254 and 256 produce 60 and 80% signals. At 20% non-linearity, for example, the linear rate is in effect 80% of the time, and the non-linear rate 20% of the time. It is to be noted that the linear or non-linear rate clock referred to is that available from NAND gate 164 in FIG. 6 which receives pulses from both one-shot 152 and one-shot 246.

Turning now to FIG. 7, the binary coded decimal input number to rate multipliers 222 and 224 in FIG. 6, or the rate control signals as they may be referred to, are generated by the circuitry shown therein. Operational amplifier 262 is connected in a non-inverting amplifier configuration, with resistor 264 being connected in a feedback loop extending between the inverting input and the output. In conjunction with diodes 266–269 and resistors 270–273, amplifier 262 forms a digital-to-analog converter for the units digit of the value of percentage B stored in counter 124 of FIG. 4. Similarly, operational amplifier 274 is a non-inverting amplifier having resistor 276 in a feedback loop between the output and the inverting input, with a ladder network comprising diodes 278–282 and resistors 284–288 connecting to the non-inverting input. The amplifier and ladder network form a digital-to-analog converter for the tens digit and the hundreds digit of the percentage B stored in counter 126 and flip-flop 128. The contents of counters 124, 126 and flip-flop 128 are, of course, applied to the digital-to-analog converters via buslines A-I.

The analog signals developed at the outputs of amplifiers 262 and 274 are applied to quad-bilateral switch circuit 290 which controls application of the analog signals to other circuitry. Specifically, the analog signal available from amplifier 274 is applied to the A and B switches in circuit 290 and the analog signal available from amplifier 262 is applied to the input of the D switch in circuit 290. The C switch in circuit 290 is connected to plus power supply voltage. Depending upon the code supplied to circuit 290 from gradient shape switch 292, either the analog signals to bilateral switches A and D or the analog signals applied to bilateral switches B and C will be made available to the additional circuitry. Gradient shape switch 292 is a two-position switch which, in conjunction with resistors 294 and 296, provide a binary code to circuit 290 to activate the appropriate switches.

The analog representation of the tens digit from bilateral switch A of circuit 290 is applied to the plus input terminal of current comparators 298, 300, 302 and 304. The connection to comparator 298 is through a series combination of resistor 306, diode 308, and resistor 310. A similar arrangement exists for current comparator 300 and comprises resistor 312, diode 314, and resistor 316. Current comparator 302 receives the signal from bilateral switch A through a series combination of resistors 318 and 320. Similarly, comparator 304 receives the signal through a series combination of resistors 322 and 324.

The connection of the analog representation of the tens digit through bilateral switch B, when the decreasing rate of percentage B is selected, is applied to the inverting inputs of comparators 298, 300, 302 and 304. The signal is applied to comparator 298 through a series resistor combination comprising resistors 326 and 328. Similarly, the signal is applied to comparator 300 through series resistors 330 and 332. In an identical fashion, comparators 302 and 304 receive the signal through series resistor combinations respectively of resistors 334, 336 and 338, 340.

When a non-linear gradient of a decreasing rate is chosen, the positive power supply potential connected to the input of bilateral switch C of circuit 290 is supplied via the output of the switch to the positive input terminal of each current comparator through a single resistor 340, 342, 344, 346 for current comparators 298, 300, 302, and 304, respectively.

Finally, the analog representation of the units digit applied to the input of bilateral switch D is applied to the positive input terminal of the current comparators when the increasing rate non-linear programs are selected. The analog signal is applied to the plus input terminal of comparator 298 through a series resistor combination comprising resistors 348 and 350. Similarly, the signal is applied to comparator 300 through resistors 352 and 254. The signal is not applied to comparators 302 and 304, however.

The negative input terminal of each comparator is connected through a resistor 356, 358, 360, 362, respectively, to AND/OR Select circuit 364. Control inputs A and B of circuit 364 connect to gradient shape switch 292; and depending upon the desired gradient shape, either the X or the Y input signals are chosen. The $X_2$ input of circuit 364 connects to positive power supply potential and is supplied via line 366 to resisitors 356, 358, 360 and 362, when the increasing rate non-linear programs are chosen.

Before continuing further with the description of the connections relating to circuit 364, it should be pointed out that because each comparator 298, 300, 302, and 304 is a current comparator; if more current flows into the minus input terminal than into the plus input terminal, the output voltage will be at ground potential. If more current flows into the plus input terminal than into the minus input terminal, the output voltage goes up to a level sufficient to represent a logic "1" value. Accordingly, as the analog representation of the percentage B in counters 124, 126 and in flip-flop 128 change, the current being supplied into the various input terminals of the current comparators will also change, effecting a change in the output signals available therefrom.

Returning to Selector circuit 364, in addition to the connections already described, Selector circuit 364 also receives as an input signal the output of current comparator 298, which is applied to the $X_0$ input. The $X_3$ input and the $Y_3$ input are not utilized. The $X_1$ and $Y_0$ inputs are both connected to the output of current comparator 302, and the $Y_1$ input is connected to the output of current comparator 304. If an increasing rate of change gradient is desired, a logic "1" will be applied to the A control input of selector circuit 364 and a logic "0" will be applied to the B control input via pull-down resistor 296. With those inputs applied to Selector 364, the output of current comparator 302 will be available at the $Z_1$ output. Similarly, the output of current comparator 298 will be available at the $Z_0$ output.

If the control input values are changed, as is the case when a decreasing rate gradient shape is selected, the output of current comparator 302 will be available to the $Z_0$ output; and the output of current comparator 304 will be available from the $Z_1$ output. Also, the voltage applied to resistors 356, 358, 360 and 362 will be at ground potential, rather than positive power supply potential, which is available to those resistors when an increasing rate gradient shape is selected.

Referring now to FIG. 6 in conjunction with FIG. 7, the binary coded decimal input number to rate multipliers 222 and 224 will be observed to originate from current comparators 298, 300, 304 and from AND/OR Select circuit 364. The interconnection between these two groups of circuitry is via the interconnect lines 226, 228, 230, 234 and 236. It will be appreciated that as the percentage B value stored in counters 124, 126 and in flip-flop 128 changes, the analog representation thereof will change accordingly. The output signals available from the current comparators will be changed, thereby effecting a change in the binary coded decimal input number to the rate multipliers.

With an increasing rate of change gradient shape selected, and with the percentage B at zero, the outputs of all current comparators are at a logic "0". The output of current comparator 298 goes to a logic "1" when the units digit reaches a count of one, and is kept high by the tens digit when the units digit reverts to zero, as at the 10, 20, 30 . . . etc. counts. The output of comparator 300 goes to a logic "1" when the units digit reaches a value of three, and the output of comparator 302 goes to a logic "1" when the tens digit reaches two. The output of comparator 304 goes to a logic "1" when the tens digit reaches five. It will be noted that these numbers, which represent the percentage B then existing in counters 124 and 126, are the break points for the increasing rate non-linear curve of FIG. 2. If a decreasing rate non-linear curve were desired, the break points would correspond to the 20, 40, 60 and 80 percent B points.

With the output of each comparator at a logic "0", only lines 232 connected to rate multiplier 222 and line 237 connected to rate multiplier 224 are at a logic "1". With this input code, rate multiplier 222 produces two output pulses for each 10 input pulses received; rate multiplier 224 produces one output pulse for each 10 input pulses received from rate multiplier 222. The ratio of output pulses available from rate multiplier 224 to input pulses supplied to rate multiplier 222 over line 146 is 0.02. When the percentage B units digit reaches a value of one and the output of comparators 298 goes to a logic "1", both lines 232 and 234, connecting to rate multiplier 222, and lines 236 and 237, connecting to rate multiplier 224, are at a logic "1". With this input code, each rate multiplier produces three output pulses for every 10 input pulses received for a combined ratio of output pulses to input pulses of 0.09. Further, when the output of current comparator 300 goes to a logic "1", that signal is applied via line 230 to rate multiplier 222, resulting in that device producing seven output pulses for every ten input pulses received and resulting in a ratio of the output pulses to the input pulses of 0.21. Next, line 228 goes to a logic "1". Under these conditions, rate multiplier 222 produces nine pulses for every ten pulses received, and rate multiplier 224 produces seven pulses for every 10 pulses received, which yields a combined ratio of 0.63. At the next break point, lines 228, 230, 232, 234, 236 and 237 are all at a logic "1" and both rate multipliers provide 10 pulses for every ten pulses received, which provides a ratio of output pulses to input pulses of 1.0.

The pulses available from rate multiplier 224, as described previously, are passed on to NAND 164 which provides the train of pulses to the frequency division circuits that supply the final % B RATE CLK. It will be observed that the train of pulses received by the frequency division circuits will be acted upon subject to the position of rate switch 174. The effect of the percentage B per minute chosen by rate switch 174 is that the elasped time from 0 to 100 percent B will vary, as it is a function of the percent B per minute chosen. Data for the plots of FIG. 2 were obtained at 5 percent per minute giving total gradient times of about 20 minutes. At any other selected percentage B per minute, the gradient shape would be the same as in FIG. 2; however, the time scale would be extended or contracted.

Referring briefly once again to FIG. 4 and the output control logic 33 illustrated therein, an additional logic input to NOR gate 72 is that from percentage B end of range decoding circuitry comprising NOR gates 368, 370 and NAND gate 372, along with NOR gate 374. The combination logic of gates 368, 370 and 372 detect the existance of all logic "0's" in the binary representations of the units and tens digits of the percentage B value in counters 124, 126. When all zeroes are detected, gate 372 has a logic "0" at its output, which is applied as an input to NOR gate 374. If the value of percentage B is zero percent, the L100 line from the Q output of flip-flop 128 will be at a logic "0", and the output of NOR gate 374 will be a logic "1", thereby disabling NOR gate 72. However, if the L100 line is at a logic "1", as when the % B value to be produced is 100%, the output of NOR gate 374 is a logic "0", permitting driver transistor 54 to be turned-on. Also, if the percentage B value is any number from 1-99%, the units and tens digits binary representations will not be all logic "0's" and NOR gate 72 will be enabled.

Figure 8:
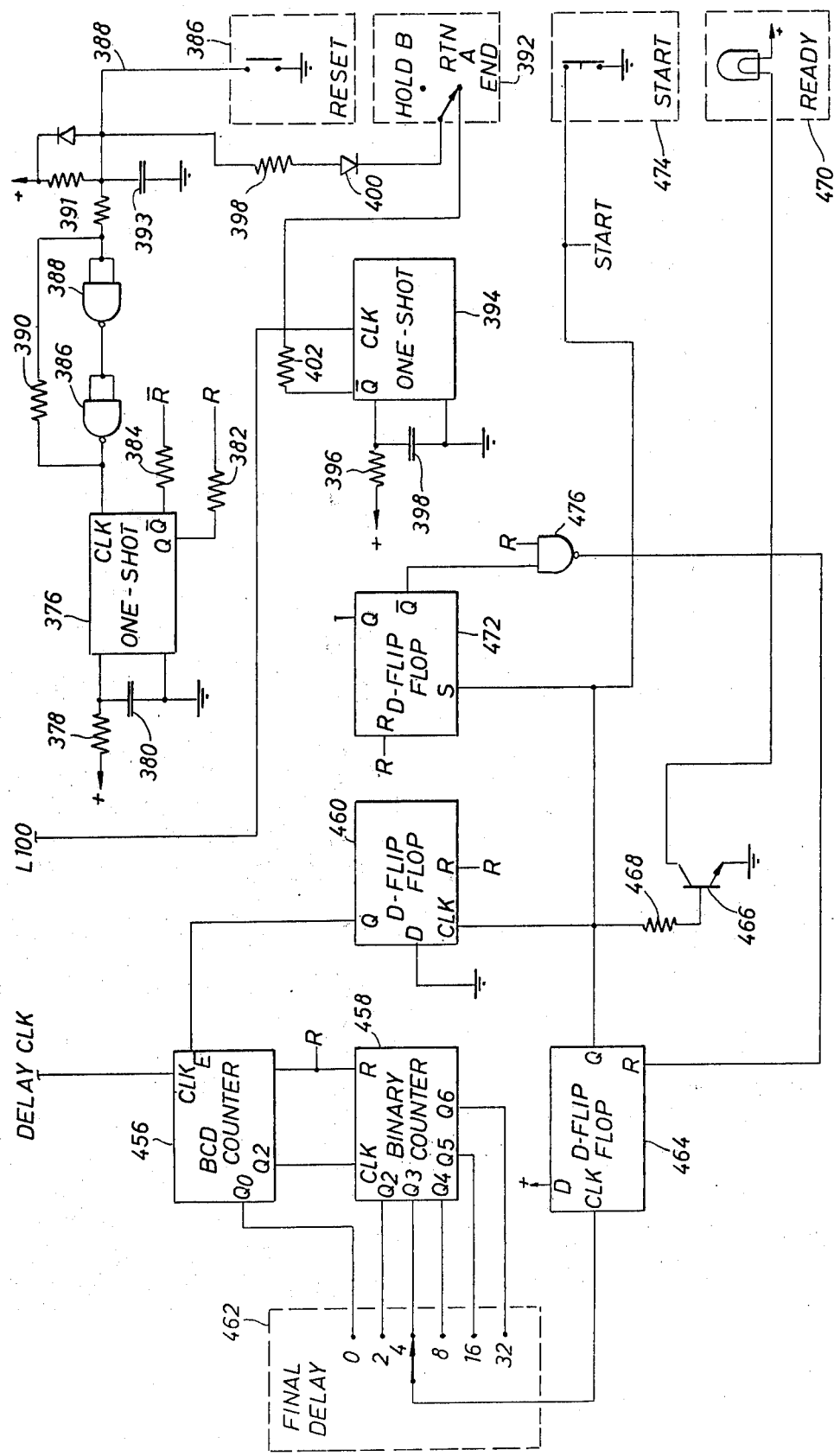

Referring next to FIG. 8, control circuitry for enabling and intializing the remaining circuitry is presented. The control circuitry is centered around one-shot 376 which generates rest signals for the counters throughout the circuitry. Specifically, a pulse, the width of which is determined by resistor 378 and capacitor 380, is available from the Q and $\overline{Q}$ outputs of one-shot 376 through resistors 382, 384. The reset pulse is generated in a number of situations.

First, the reset pulse can be initiated when the reset button 386 is pushed. When that button is pushed, line 388 is connected through the reset-button to ground. Previously, this line had been at approximately the power supply potential because of its connection through resistor 390 to the power supply. Grounding of line 388 causes a triggering signal to be applied to the clock input of one-shot 376. The triggering transistion is supplied from the series combination of NAND gates 386, 388 with a small amount of hysteresis resulting from positive feedback provided by resistor 390.

The initiation of reset signals will also occur when percentage B reaches 100%, if the end switch 392 is in the return to A position. Circuitry providing this operation is comprised of one-shot 394 which has its clock input connected to the L100 line. During the linear and non-linear gradient modes of operation, when the percentage B has reached 100%, line L100 will go to a logic "1" triggering one-shot 394. A pulse having a duration defined by the values of resistor 396 and capacitor 398 is produced. The pulse is actually a negative-going transition of a previously high logic level. Therefore, the $\overline{Q}$ output of one-shot 394 acts as a current sink and pulls line 388 down to near ground potential through resistor 398, diode 400 and resistor 402. However, if it is desired that the solvent programmer maintain and continue to supply a 100% B mixture, placement of END switch 392 in the HOLD B position will prohibit automatic resetting of the various portions of the control module circuitry.

The reset pulses are available as both positive-going and negative-going pulses, designated as R and $\overline{R}$, respectively. Counters 124 and 126 in FIG. 4 are preset by NAND gate 404 through resistor 406 to the initial percentage of B set on switch 84. NAND gate 404 receives the $\overline{R}$ reset pulse. The other input of NAND gate 404 serves to force the units and tens counters to zero when the hundreds counter reaches a count of "1". The positive voltage to the units and tens digital switches is likewise removed when the "1" count of the hundreds counter exists. If a reset condition is initiated, $\overline{R}$ goes low, causing a reset pulse to be delivered to counters 124 and 126. During operation, the second input of NAND gate 404 is maintained at a logic "1", until the $\overline{Q}$ output of flip-flop 128 goes low, whereupon counters 124 and 126 are again preset.

Flip-flop 128 is reset through NOR gate 412 having a first input lead connected through resistor 414 to ground and to the $\overline{R}$ reset line. The second input of NOR gate 412 connects to digital switch 84 in the manner illustrated. The manner in which flip-flop 128, in conjunction with NOR gate 412, operates will be apparent.

Figure 9:
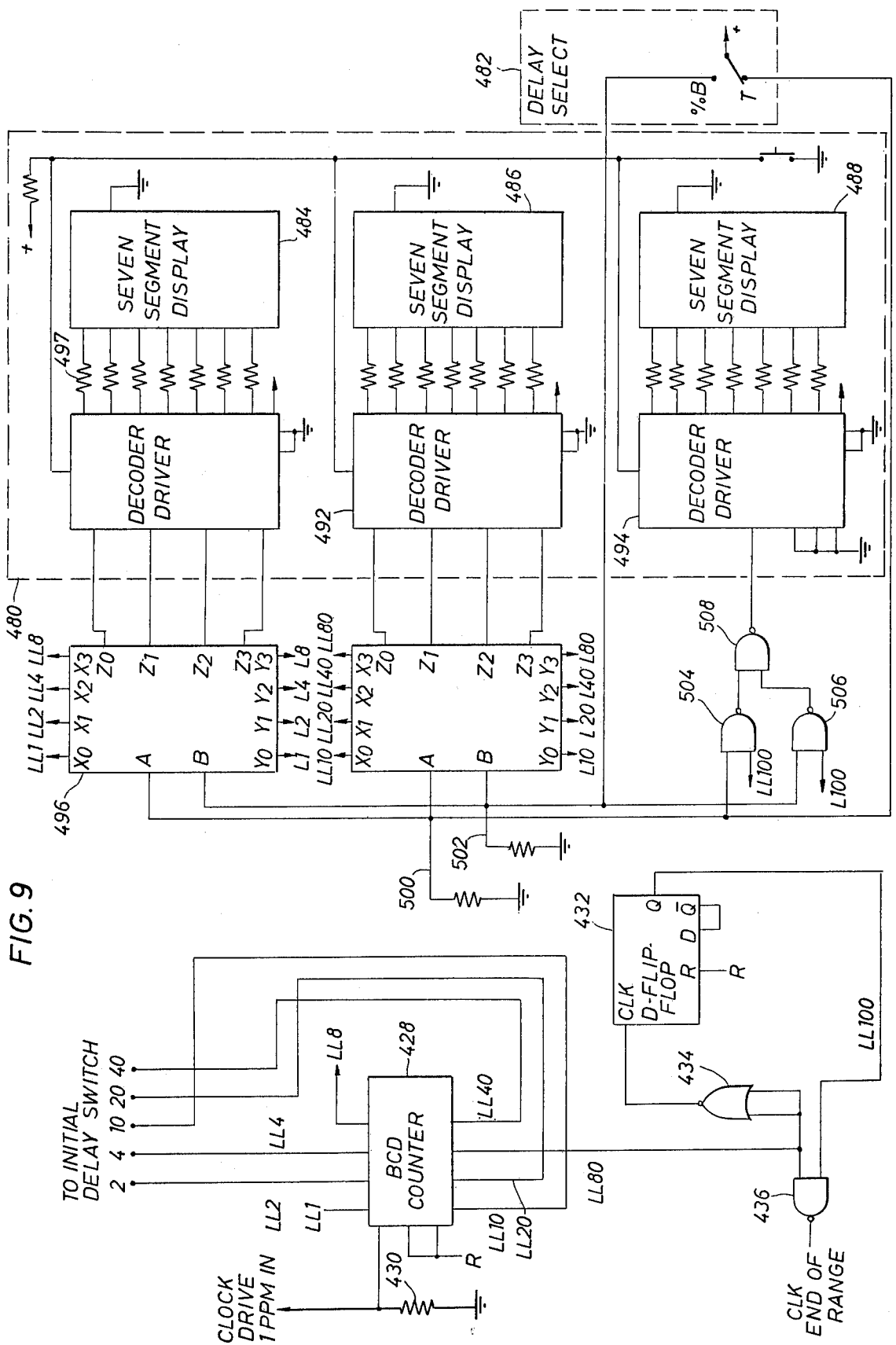

Referring now to FIGS. 5 and 9 in conjunction, the elapsed time counter for timing the period of time in which solvent programmer 10 is in operation. A 3.3 Hz signal available from BCD counter 102, shown in FIG. 5, is applied to flip-flop 420 which divides the frequency by a factor of two and provides a 1.67 Hz signal from the Q output. The signal is applied to cascaded BCD counters 422, 424, where the signal is further divided down by a factor of 10 in each counter. The signal available from counter 424 through resistor 426 is a one pulse per minute signal. This signal is applied to resistor 430 and BCD counter 428 (FIG. 9). Counter 428 counts at the rate of one count per minute and provides a binary coded decimal representation of the units and tens digits of the elapsed time. The hundreds designation is provided by flip-flop 432 receiving clock pulses through NOR gate 434. NAND gate 436 provides an end of range clock when an elapsed time of 180 minutes has been reached.

The end of range clock is applied to NAND gate 438 (FIG. 5). At the occurrence of the end of range clock, the BCD counter 424 is disabled and prevented from passing further pulses, into the elapsed time counter ceases to count. The binary coded decimal representation of the elasped time digits are provided to the display circuitry in a manner that will be described more fully hereinafter.

The initial delay circuitry permits a certain time period to be programmed into the solvent programmer to inhibit operation of the apparatus until the time has elapsed. The initial delay is achieved through the use of flip-flop 440 which is reset by the reset pulse, making the $\overline{Q}$ output high. This logic level is applied to NOR gate 442, causing its output to assume a logic "0" which is further applied to NAND gate 132. Application of this signal to NAND gate 132 inhibits passage of the 333 Hz signal to the rate circuits. After the delay determined by the setting of the initial delay switch 444, flip-flop 440 is clocked, making the $\overline{Q}$ output go low and enabling the passage of the 333 Hz signal through NAND gate 132.

It should also be discussed here that the Q output of flip-flop 440 is applied through resistor 446 to transistor 448 which serves as the pump control relay driver. When the Q output of flip-flop 440 goes high, with the pump control switch 450 in the on position, current is drawn through pump control switch 450 in the on position, current is drawn through pump control relay coil 452. This results in the contacts 454 of the pump control relay to be closed changing the speed of the continuous pump in the solvent module.

The final delay circuitry enables the user of the solvent programmer apparatus to select a delay period after conclusion of a gradient run before another run can be started. For example, if a gradient is run and a final delay time of eight minutes is selected with return to solvent A, the device will run through the program gradient and return to the initial condition selected immediately after reaching 100% B. However, there will be a required wait of eight minutes before another gradient run can be started. The use of final delay insures proper cleaning out of the system with the initial solvent and desired reconditioning of the chromatographic system to the same initial point.

The final delay circuitry is illustrated in FIG. 8 a BCD counter is clocked by the delay clock available from BCD counter 442 (FIG. 5). The output signal available from $Q_2$ output of counter 456 is applied to binary counter 458. Enablement of counter 456 to operate is under the direction of the Q output of flip-flop 460. When enabled, counter 456 and counter 458 are allowed to count with a signal selected in accordance with the setting of final delay switch 462 being used to clock flip-flop 464.

The reset pulse resets counters 456, 458 and flip-flop 464. The reset pulse resets flip-flop 460. After a delay period selected by the final delay switch 462, flip-flop 464 is clocked, driving the Q output to a logic 1. This level applied to the base of transistor 466 through resistor 468 turns the device on, lighting the ready indicator light 470. Flip-flop 460 is clocked to establish a logic "0" on the Q output, which inhibits further counting by counter 456. Flip-flop 472 having been reset has the Q output at a low logic level, inhibiting via NAND gate 438 (FIG. 5) generation of the one-pulse per minute output from BCD counter 424. Operation of the start button 474 ungrounds the set input of flip-flop 472, which was previously pulled to a high level by flip-flop 464. Counter 424 is then released and allowed to count, and flip-flop 464 is reset via NAND gate 476.

The display 47 for controller 28 is generally designated by the reference numeral 480 in FIG. 9. The display is a digital readout, providing either the percentage B being created by the solvent programmer, or if desired, the elapsed time in minutes since the operation of the start button. This selection is made by the proper setting of display select switch 482. Since a maximum readout of 180 minutes is available, if a longer period of time has elapsed, the display will hold at 180 minutes. Similarly, since the maximum percentage B in a mixture is 100%, display 480 will so indicate. Generally, display 480 comprises three seven-segment display units 484, 486 and 488. These units are a common cathode LED numeric display, and receive driving signals from a separate individual decoder drivers 490, 492 and 494. The driving signals to the display units are via identical resistors 496.

Decoder drivers 490, 492 and 494 each receive a binary coded decimal input that is representative of one digit of the three digit display. For example, decoder driver 490 receives the units representation, decoder driver 492 receives the tens digit representation, and decoder driver 494 receives the hundreds unit representation. Since both the percentage B and the elapsed time must be made available to be displayed on the display units, and/or select circuits 496 and 498 are utilized. Select circuit 496 receives the binary coded decimal representation of the units digit for both the percentage B and the elapsed time. Select circuit 498 receives the binary coded decimal representation of the tens digit of both the percentage B and the elapsed time. Depending upon whether the display select switch 482 is in the percentage B or in the lapsed time position, the A and B control lines 500, 502 will establish a code that selects either the elapsed time or the percentage B digital representations. The decoded driver for the hundreds digit in the display receives a signal from and/or combination logic comprising NAND gates 504, 506 and 508. Again, depending upon the display select switch 482 either NAND gate 504 or NAND gate 506 is enabled, permitting the binary representation of either the elapsed time or the percentage B digit to be supplied to decoder driver 494.

| LIST OF PREFERRED COMPONENTS | |
|---|---|
| * Resistors are ¼ W, 5% in ohms; and Capacitors are in microfarads. | |
| FIG. 4 | |
| Resistors | |
| 80, 82, 86a-i, 106, 130, 414 | 1 Meg |
| 114, 120 | 27 k |
| 406 | 470 k |
| Capacitors | |
| 116, 122 | 0.1 |
| I.C.'s | |
| NOR gates 70, 72, 74 | CD4025 |
| NOR gates 368, 370 | CD4002 |
| NOR gates 374, 76, 412 | CD4001 |
| NAND gates 372, 404 | CD4011 |
| One-Shot 112, 118 | MC14528 |
| U/D Counters 108, 110, 124, 126 | CD4029 |
| BCD Counter 104 | MC14518 |
| Diodes 56, 60, 64, 68 | IN914 |
| Transistors 54, 58, 62, 66 | MJE1100 |
| FIG. 5 | |
| Resistors | |
| 90 | 2.2 k |
| 96 | 10k pot. |
| 94 | 240 k |

LIST OF PREFERRED COMPONENTS
*Resistors are ¼ W, 5% in ohms; and Capacitors are in microfarads.*

| | |
|---|---|
| 100 | 47 k |
| 142 | 1 Meg. |
| 257, 258, 259, 260, 426 | 6–8 k |
| 446 | 10 k |
| Capacitors | |
| 92 | 1800 |
| I.C.'s | |
| OSC. 88 | NE555 |
| Counter 98, 102, 422, 424 | MC14518 |
| Flip-Flop 420, 440 | CD4013 |
| NAND gates 132, 438, 254, 256 | CD4011 |
| NOR gates 134, 136, 140, 442 | CD4001 |
| Transistor 448 | MPS A40 |

FIG. 6
| | |
|---|---|
| Resistors | |
| 156, 250, 162 | 47 k |
| 242, 244, 172, 176, 180, 182, 184, 186 | 6.8 k |
| 192 | 4.7 k |
| Capacitors | |
| 154, 248 | 100 |
| I.C.'s | |
| Counter 148, 190 | MC14518 |
| One-Shot 142, 246 | MC14528 |
| Flip-Flop 150 | CD4013 |
| Flip-Flop 170 | CD4027 |
| Counter 166 | CD4017 |
| Counter 178, 240 | CD4024 |
| Rate Multiplier 222, 224 | MC14527 |
| NAND gate 164 | CD4011 |

FIG. 7
| | |
|---|---|
| Resistors | |
| 206 | 1 Meg. |
| 207 | 499k |
| 208 | 249k |
| 209 | 124k |
| 210 | 100k |
| 211 | 49.9k |
| 212 | 24.9k |
| 213 | 12.1k |
| 214 | 9.5k |
| 216 | 50 |
| 220 | 100 |
| 270, 284 | 4.99 Meg. |
| 271, 285 | 2.49 Meg. |
| 272, 286 | 1.24 Meg. |
| 273, 287 | 619k |
| 288, 264, 276 | 4.99k |
| 326, 206, 248, 330, 312, 352, 334, 338, 322 | 24.9k |
| 328 | 665k |
| 296, 294, 346, 344, 342, 340, 356, 358, 360, 362 | 1 Meg. |
| 310, 316, 350 | 20k |
| 332, 324 | 475k |
| 354 | 210k |
| 336 | 301k |
| 318 | 25k |
| 320, 346 | 120k |
| Diodes | |
| 266–282, 308, 314 | IN914 |
| I.C.'s | |
| Comparators 262, 274, 298, 300, 302, 304 | LM3900 |
| AND/OR Select 364 | MC14519 |
| Quad Bilateral Switch 290 | CD4016 |

FIG. 8
| | |
|---|---|
| Resistors | |
| 378, 396 | 2.2 Meg. |
| 382, 384, 398, 468 | 10k |
| 390 | 10 Meg. |
| 391 | 100k |
| 402 | 6.8k |
| Capacitors | |
| 380, 298 | 0.1 |
| 393 | 10 |
| I.C.'s | |
| Counter 456 | MC14518 |
| Counter 458 | CD4024 |
| One-Shot 376, 394 | MC14528 |
| Flip-Flop 464, 460, 422 | CD4013 |
| NAND gates 386, 388, 476 | CD4011 |
| Transistor 466 | MPSA14 |

FIG. 9
| | |
|---|---|
| Resistors | |
| 497 | 1k |
| 500, 502, 430 | 1 Meg. |
| I.C.'s | |
| 490, 492, 494 | MC14511 |
| 496, 498 | MC14519 |
| NAND gates 504, 506, 508, 436 | CD4011 |
| NOR gate 434 | CD4001 |
| Counter 428 | MC14518 |
| Flip-Flop 432 | CD4013 |

The foregoing description of the invention has been directed to a particular perferred embodiment in accordance with the requirements of the Patent Statute and for purposes of explanation and illustration. It will be apparent, however, to those skilled in this art that many modifications and changes in the apparatus may be made without departing from the scope and spirit of the invention. For example, rather than using a down counter preset from the contents of the data storage means, an up counter could be used and connected along with the data storage means to comparison logic that compares the count of the counter bit for bit with the binary value stored in the data storage means. Accordingly, when the counter reaches the count, the value of which matching the contents of the data storage means, an output signal may be derived and applied to the output control logic. Operation then procees as described. This and other modifications of the invention will be apparent to those skilled in this art. It is the intention in the following claims to cover all such equivalent modifications and variations as fall within the true spirit and scope of the invention.

What is claimed is:

1. In a solvent programmer apparatus that provides programmed solvent mixtures for introduction to a liquid chromatographic analyzer by accessing first and second solvents during a defined cycle of operation and proportioning the same on the basis of the time within the cycle that each solvent is accessed, a controller comprising:

a time base generator for generating a timing clock signal of a prescribed frequency;

first and second counters receiving the timing signal from said time base generator;

said first counter defining a cycle of operation within which the solvents are proportioned;

data storage means for holding a representation of the percentage value of the first solvent that is to be in a mixture produced by the solvent programmer; and output control logic responsive to the count value in said first and second counters for causing the first solvent to be accessed upon said first counter reaching a prescribed count that indicates the beginning of a cycle of operation and the second solvent to be accessed for the remainder of the cycle of operation, upon said second counter reaching a prescribed count which is dependent upon the percentage value stored in said data storage means, with access of the first solvent being discontinued.

2. A controller is accordance with claim 1 further comprising:

a control interface for interfacing said output control logic to the portion of the solvent programmer apparatus that accesses the solvents.

3. A controller in accordance with claim 1 wherein the percentage value representation stored in said data storage means is intermittently increased during a solvent program run, whereby the percentage of the first solvent in a solvent mixture produced by the solvent programmer apparatus increases with time during a solvent program run.

4. A controller in accordance with claim 3 wherein: said data storage means comprises a counter that is counted up at a rate determined by the frequency of a clock supplied thereto, said counter holding the percentage value of the first solvent that is to be in a solvent mixture.

5. A controller in accordance with claim 4 further comprising:
a linear rate generator that provides a clock signal for counting up the counter in said data storage means; and
adjustment means for setting the frequency of the clock signal to a specified rate, such that the percentage value stored in said data storage means will increase linearly with time.

6. A controller in accordance with claim 4 further comprising:
a non-linear rate generator that generates a clock signal for counting up the counter in said data storage means,
said non-linear rate generator varying the frequency of clock pulses applied to the counter according to the value stored in said data storage means, such that the percentage value stored will vary non-linearly with time.

7. A controller in accordance with claim 1, further comprising:
a numerical display for providing a visual readout of the percentage value in said data storage means.

8. In a solvent programmer apparatus that provides programmed solvent mixtures for introduction to a liquid chromatographic analyzer by accessing first and second solvents during a defined cycle of operation and proportioning the same on the basis of the time within the cycle that each solvent is accessed, a controller comprising:
a time base generator for generating a timing clock signal of a prescribed frequency;
an up counter receiving the timing clock signal, said up counter defining each of a series of cycles of operation within which the solvents are proportioned;
a down counter receiving the timing clock signal, said down counter defining the portion of each cycle of operation that the first solvent is accessed;
data storage means for storing a digital representation of the percentage value of the first solvent that is to be in a mixture of the solvents produced by the solvent programmer during a cycle of operation; and
output control logic responsive to the count value in said up counter and in said down counter,
said control logic causing the first solvent to be accessed upon said up counter reaching the maximum count and the digital representation stored in said data storage means to be loaded into said down counter during each cycle, and
said control logic causing the second solvent to be accessed during the remainder of each cycle and access of the first solvent to be discontinued upon said down counter reaching the minimum count.

9. A controller is accordance with claim 8, wherein: said data storage means comprises a counter which increases the percentage value stored therein at a rate determined by the frequency of a clock signal supplied thereto; and
said controller further comprises:
a linear rate generator for providing a clock signal to be supplied to the counter in said data storage means, and
frequency divider circuitry between said linear rate generator and the counter, said divider having means for setting the division factor therethrough with the clock signal frequency being reduced to a predetermined rate, such that the percentage value will increase at a predetermined linear rate with time.

10. A controller in accordance with claim 9 further comprising:
a non-linear rate generator for providing an alternate clock signal to be supplied to the counter in said data storage means;
a gate receiving as inputs the signals from said linear rate generator and said non-linear rate generator, with the output therefrom being applied to said frequency divider circuitry; and
percent non-linearity logic for alternately enabling the generation of the clock signals from said rate generators in prescribed proportions to cause the value stored in said data storage means to be increased with a predetermined degree of non-linearity.

11. A controller in accordance with claim 10 wherein said non-linear rate generator comprises a rate-multiplier that provides an output pulse rate based upon a binary number which is derived from the contents of said data storage means.

* * * * *